(12) United States Patent
Paur et al.

(10) Patent No.: US 8,225,681 B2
(45) Date of Patent: Jul. 24, 2012

(54) DEVICE FOR MEASURING SUPERFINE PARTICLE MASSES

(75) Inventors: Hanns-Rudolf Paur, Karlsruhe (DE); Thomas Waescher, Rauenberg (DE); Sonja Muelhopt, Karlsruhe (DE)

(73) Assignee: Forschungszentrum Karlsruhe GmbH, Karlsruhe (DE)

( * ) Notice: Subject to any disclaimer, the term of this patent is extended or adjusted under 35 U.S.C. 154(b) by 341 days.

(21) Appl. No.: 12/532,474

(22) PCT Filed: Feb. 27, 2008

(86) PCT No.: PCT/EP2008/001535
§ 371 (c)(1),
(2), (4) Date: Sep. 22, 2009

(87) PCT Pub. No.: WO2008/116540
PCT Pub. Date: Oct. 2, 2008

(65) Prior Publication Data
US 2010/0083737 A1    Apr. 8, 2010

(30) Foreign Application Priority Data
Mar. 23, 2007 (DE) .......................... 10 2007 013 938

(51) Int. Cl.
*G01G 9/00* (2006.01)
(52) U.S. Cl. ........................................... 73/865
(58) Field of Classification Search .................. None
See application file for complete search history.

(56) References Cited

U.S. PATENT DOCUMENTS

| | | | |
|---|---|---|---|
| 3,561,253 A | 2/1971 | Dorman | |
| 3,805,591 A * | 4/1974 | Willis et al. | 73/24.03 |
| 3,981,264 A * | 9/1976 | Smith et al. | 346/33 R |
| 5,604,335 A * | 2/1997 | Isahaya | 177/210 FP |
| 6,205,842 B1 * | 3/2001 | Patashnick et al. | 73/28.01 |
| 6,510,727 B2 | 1/2003 | Reiter et al. | |
| 7,115,229 B2 | 10/2006 | Zenhausern | |
| 2004/0028620 A1 | 2/2004 | Monnot et al. | |
| 2005/0170499 A1 | 8/2005 | Mohr et al. | |
| 2006/0086174 A1 * | 4/2006 | Korpi | 73/24.01 |
| 2008/0202926 A1 * | 8/2008 | Hontsu et al. | 204/400 |

FOREIGN PATENT DOCUMENTS

| | | |
|---|---|---|
| DE | 19801763 A1 | 7/1999 |
| DE | 10061976 A1 | 6/2001 |
| EP | 1174496 A2 | 1/2002 |
| WO | WO-0241973 A1 | 5/2002 |
| WO | WO-03076599 A2 | 9/2003 |

* cited by examiner

*Primary Examiner* — Robert R Raevis
(74) *Attorney, Agent, or Firm* — Leydig, Voit & Mayer, Ltd.

(57) ABSTRACT

A device for measuring superfine particle masses including a quartz oscillator and an exposure system having at least two measuring chambers. Each of the at least two measuring chambers has a same geometry, a deposition surface for particles, and an aerosol feed directed at the respective disposition surface configured to feed an aerosol onto the respective deposition surface. At least one of the respective deposition surfaces is disposed on the quartz oscillator.

12 Claims, 3 Drawing Sheets

Figure 1:
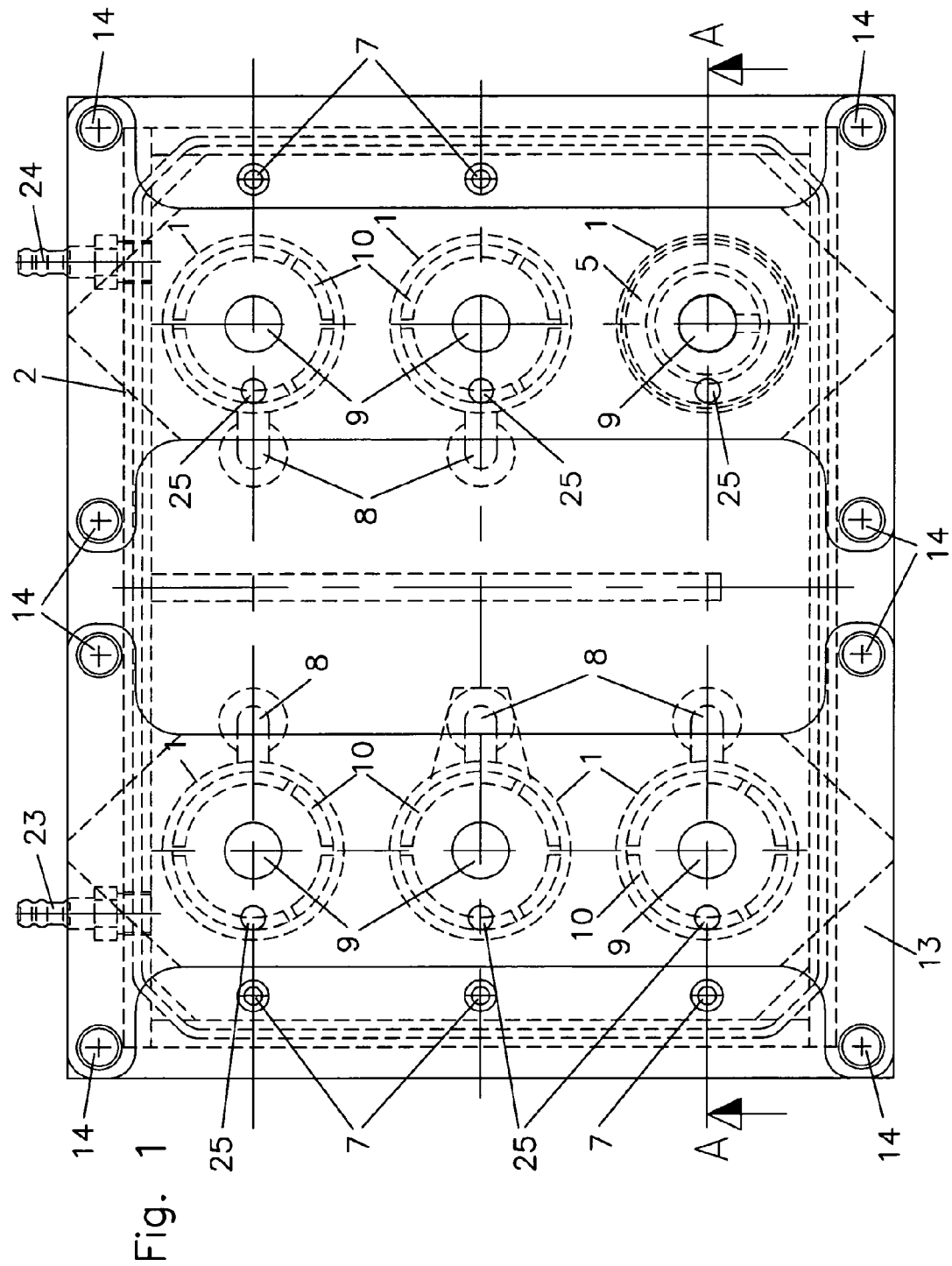

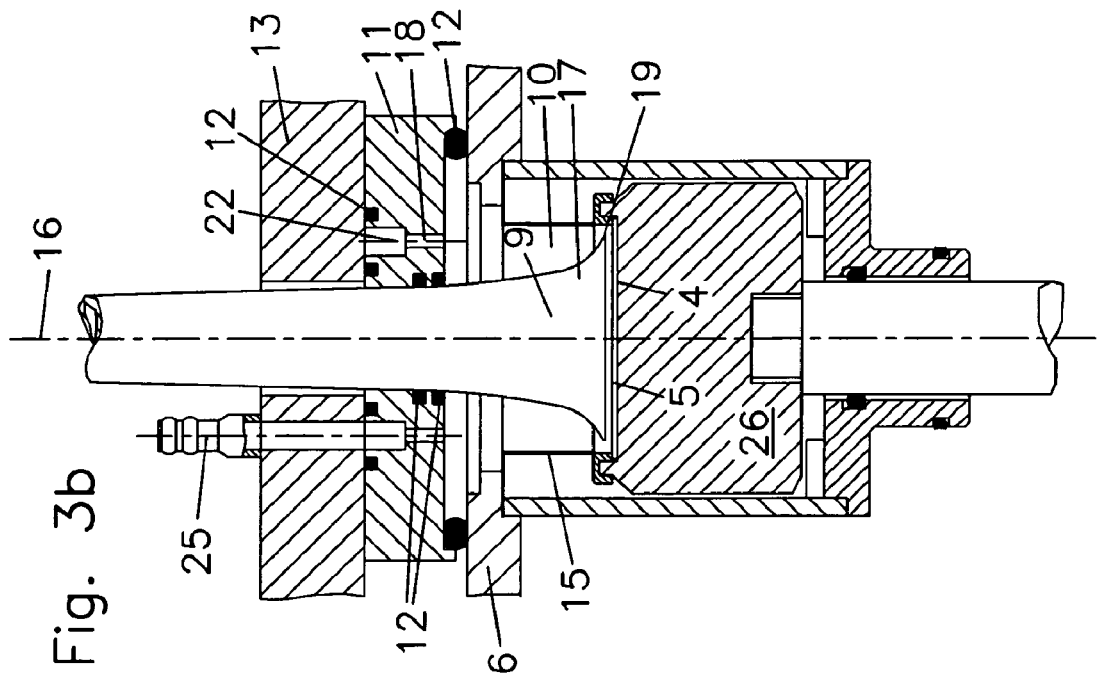
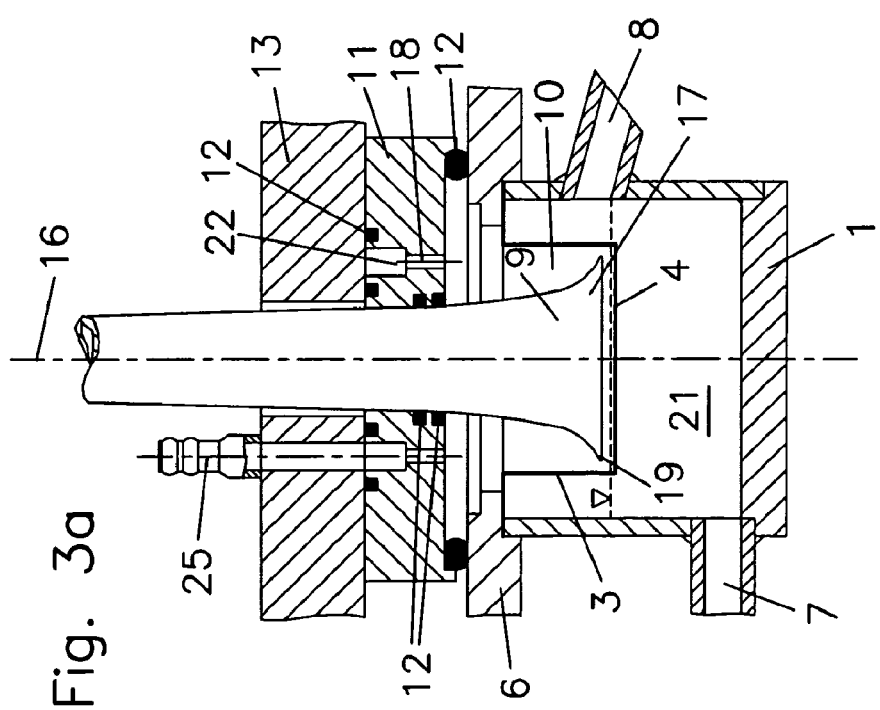

DEVICE FOR MEASURING SUPERFINE PARTICLE MASSES

CROSS REFERENCE TO PRIOR APPLICATIONS

This application is a U.S. National Phase application under 35 U.S.C. §371 of International Application No. PCT/EP2008/001535, filed on Feb. 27, 2008 and which claims benefit to German Patent Application No. 10 2007 013 938.3, filed on Mar. 23, 2007, both incorporated by reference herein. The International Application was published in German on Oct. 2, 2008 as WO 2008/116540 A1 under PCT Article 21(2).

FIELD

The present invention relates to a device for measuring superfine particle masses, for example, on a bioassay.

BACKGROUND

Devices for measuring superfine particle masses are used for detecting and/or analyzing emissions from aerosols or dust in general. Of particular interest in the first instance are the purely physical deposition kinetics on certain surfaces (deposition surfaces) resulting from adsorption. In this context, the superfine particle masses can also diffuse into the surface, i.e., be taken up and intercalated in the course of a physical diffusion process (absorption). Chemical and physical interactions of the superfine particles on or in the deposition surfaces can be detected using these devices and quantified through application of additional morphological, physical or chemical analysis methods of the known type.

Another field of application of the aforementioned devices is the in vitro analyses of superfine dust deposits or biochemical or biophysical interactions on bioassays, i.e., on biological or biologically active surfaces. Analyses of this kind constitute a useful and, due to ethical considerations, preferable way to supplement epidemiological investigations (using statistical data) or in vivo analyses on living beings (for example, tests on animals), such as to make toxicological assessments of atmospheric dust and pollutant loads, for example, at contaminated workplaces, in traffic or in industrial installations.

Importance is accorded to emissions analysis in the context of what is generally referred to as superfine particle loads. Superfine particles, also known as nanoparticles, refer to particles having diameters in the submicrometer region, i.e., of a few nanometers up to maximally one micrometer. Due to their very large surface area-to-mass ratio in comparison to larger particles or solids, superfine particles exhibit an often completely different and often not yet fully investigated and thus unknown property profile and reaction behavior.

In recent years, epidemiological and toxicological investigations have revealed, for example, that increased emissions of such superfine particles are accompanied by a significant increase in the occurrence of various diseases, such as heart/circulatory disturbances or chronic respiratory difficulties. To provide a comprehensive emissions protection for the population, new boundary limits were derived therefrom. However, under the present technical and economic boundary conditions, these would require drastic measures and are not observable.

However, a device of the aforementioned type permits the analyses of superfine particle loading that is more goal-oriented, whereby the mentioned measures are also able to be introduced in a more targeted and thus efficient manner.

Therefore, there is no longer a need for comprehensive measures that are difficult to implement.

In vitro investigations for measuring superfine particle masses, as well as their toxicological effects on living organisms, often utilize biological model structures, such as cell cultures, for example, on a suitable cultivation support structure, such as a Petri dish or, in the case of bacterial cultures, a nutrient medium. The structures are exposed as an open layer to the aerosol or to a suspension of a carrier fluid (gas or liquid) and the superfine particles.

DE 198 01 763 C2 describes a culture device for cultivating cells or tissue components where the cell cultures are grown on porous membranes in Transwell inserts. For the aforementioned in vitro investigations, the nutrient solution on the top side of the planar cultures is removed to permit application of an aerosol, while the space underneath the membrane is continuously rinsed with fresh nutrient medium for purposes of supplying the cells and avoiding an accumulation of toxic metabolic products. The system has already established itself under the CULTEX® brand name in many areas of inhalation research, such as in the investigations of Diesel soot and cigarette smoke.

However, the in vitro investigations known till now are based exclusively on time-integral measurements. In the same way as the mentioned in vivo investigations, the cell cultures are investigated at intervals, i.e., only after a specific test duration has elapsed. Fluctuations in an aerosol emission and the temporary biochemical effects thereof on a cell culture can often not be understood or can only be very imprecisely understood, for example, on the basis of individual tests.

SUMMARY

An aspect of the present invention is to provide a device for measuring superfine particle masses which also detects the adsorption or absorption kinetics, and as a biological system, additionally or alternatively the toxi- or pharmacokinetics.

In an embodiment, the present invention provides a device for measuring superfine particle masses including a quartz oscillator and an exposure system having at least two measuring chambers. Each of the at least two measuring chambers has a same geometry, a deposition surface for particles, and an aerosol feed directed at the respective disposition surface configured to feed an aerosol onto the respective deposition surface. At least one of the respective deposition surfaces is disposed on the quartz oscillator.

BRIEF DESCRIPTION OF THE DRAWINGS

The present invention is described in greater detail below on the basis of embodiments and of the drawings in which:

FIG. 1: a plan view of a specific embodiment having six exposure chambers;

FIG. 2: a sectional representation of the device (in accordance with FIG. 1 along the line characterized by A-A); as well as FIGS. 3*a* and *b*: detailed sectional representations of the exposure chambers shown in FIG. 2.

DETAILED DESCRIPTION

The present invention relates to a device for measuring superfine particle masses that is conceived for investigating the emission of superfine particles onto deposition surfaces, for example, by sedimentation, diffusion, adsorption or absorption, or other physical or chemical binding.

An embodiment of the present invention includes means or method steps for detecting an emission of the particles onto deposition surfaces not only integrally, but also in a time-resolved manner. The quantity of emitted particles deposited is continuously and, for example, also quantitatively recorded. As a result, a deposition process flow may be monitored on-line. The thus attainable advantage of an on-line recording of this kind resides not only in the real-time acquisition of the particle deposition on the deposition surfaces, but also in the real-time processing of these deposition rates as measured variables for test-engineering control commands, for example, for manipulating test procedures, for alarm systems or for supplementary measurements, as well as for safety-critical measures.

In an embodiment of the present invention, the device includes an exposure system having at least two measuring chambers (exposure chambers) having identical geometries, in each of which a deposition surface is provided for particles, and each having an aerosol feed directed at the same for feeding an aerosol onto the deposition surface.

Superfine dust or nanoparticles are characterized by a large specific surface area. This significantly promotes a strong adhesion of these particles to planar surfaces, such as the deposition surfaces referred to, mostly due to van-der-Waals forces. Other adhesion mechanisms, such as bonding or surface tension effects, may also play a role. They are, however, less important and, in the present context of fine dust or nanoparticles, are negligible. Within the framework of the present invention, however, it became apparent that this adhesion between superfine dust and the deposition surfaces is substantially determined by the surface topography and not or only minimally by the surface material. Therefore, when the quantities of superfine dust or nanoparticles deposited on a plurality of deposition surfaces are compared, it may be ascertained that the surface material advantageously plays only a minor role. However, a more pronounced influence of the material on the deposition behavior occurring in individual cases, for instance due to the aforementioned additional adhesion mechanisms, may be reliably correlated to fixed correction factors or functions. For that reason, the present invention provides for at least two measuring chambers having identical geometries, these deposition surfaces being identical in their surface topographies (surface condition) and dimensions, but being able to differ in their surface materials.

In an embodiment of the present invention, the deposition surfaces are not only geometrically identical, but are also identical in their surface materials. The measuring chambers can each have, for example, identical aerosol feeds directed onto the deposition surfaces or identical suction removal. The assumption here is that each of these identical aerosol feeds taps the same source of superfine particles. The aim of these embodiments is a comparable and most identical possible deposition of the same superfine particle quantities onto each of the deposition surfaces.

At least one of the deposition surfaces on a quartz oscillator is conceived as a microbalance, and compared to the other deposition surfaces that are not equipped with a quartz oscillator, these surfaces not assuming any other deviating position in the exposure chamber. The masses of the superfine particles bound to the deposition surface may thus be advantageously determined not only during a test time period. The superfine particle masses on the remaining deposition surfaces may also be estimated because of the identical configurations in the exposition chambers and thus because of a transferability to the other exposure chambers having identical geometries.

If the exposure chambers exhibit differences among themselves, such as, for example, geometric or aerodynamic differences, a fundamental transferability of the depositions is nevertheless given. In this context, deviations in the measuring results and thus measuring errors may be minimized or corrected where necessary by using fixed correction factors or variable correction functions (correlation relations) determined empirically on the basis of comparative tests.

In an embodiment of the present invention, all of the deposition surfaces are equipped with quartz oscillators to permit a more extensive adaptation of the deposition surfaces in terms of identical surface oscillation states and thus of the deposition dynamics for superfine powder masses. This embodiment also allows comparative determinations to be made regarding the masses on the oscillating deposition surfaces and thus also permits an early detection of faulty exposure chambers (quality monitoring).

The determination of the masses may be carried out without interruption or as one or more individual measurements, the driving of the quartz oscillator and the process of acquiring data therefrom, can, for example, take place in a computer-controlled operation.

The measures mentioned advantageously permit an on-line acquisition of the actual, deposited superfine particle masses, directly in the exposure system. There is no need for additional measuring units. Conversion algorithms or model considerations are thus eliminated as sources of inaccuracies or errors. The use of a direct measuring concept makes the device very reliable, simple in design and, therefore, cost-effective. There is no need for a chemical or radioactive marking of the aerosol or of the superfine particles for purposes of a quantitative detection.

The specific embodiment shown in FIG. 1 has an arrangement of six exposure chambers 1 for the through-flow of an aerosol in a common housing 2. The geometries of the through-flow volumes for the aerosol are, for example, identical for all six exposure chambers. Five of the six exposure chambers are equipped with one Transwell insert 3 each as a deposition surface 4 (cell culture surface, for example on a polycarbonate membrane), while, in the sixth exposure chamber, deposition surface 4 is situated on a quartz oscillator 5 as a sensing element of a quartz microscale. The deposition surface can, for example, be formed directly by the surface or the electrode of the quartz oscillator. As a quartz microscale, a QCM200 type system of the firm Stanford Research Systems, Inc., Sunnyvale, Calif. was used representatively for other comparable systems. In addition, a line characterized by A-A is included in FIG. 1 and serves as a sectional plane for the representation in accordance with FIG. 2.

Figure 2:
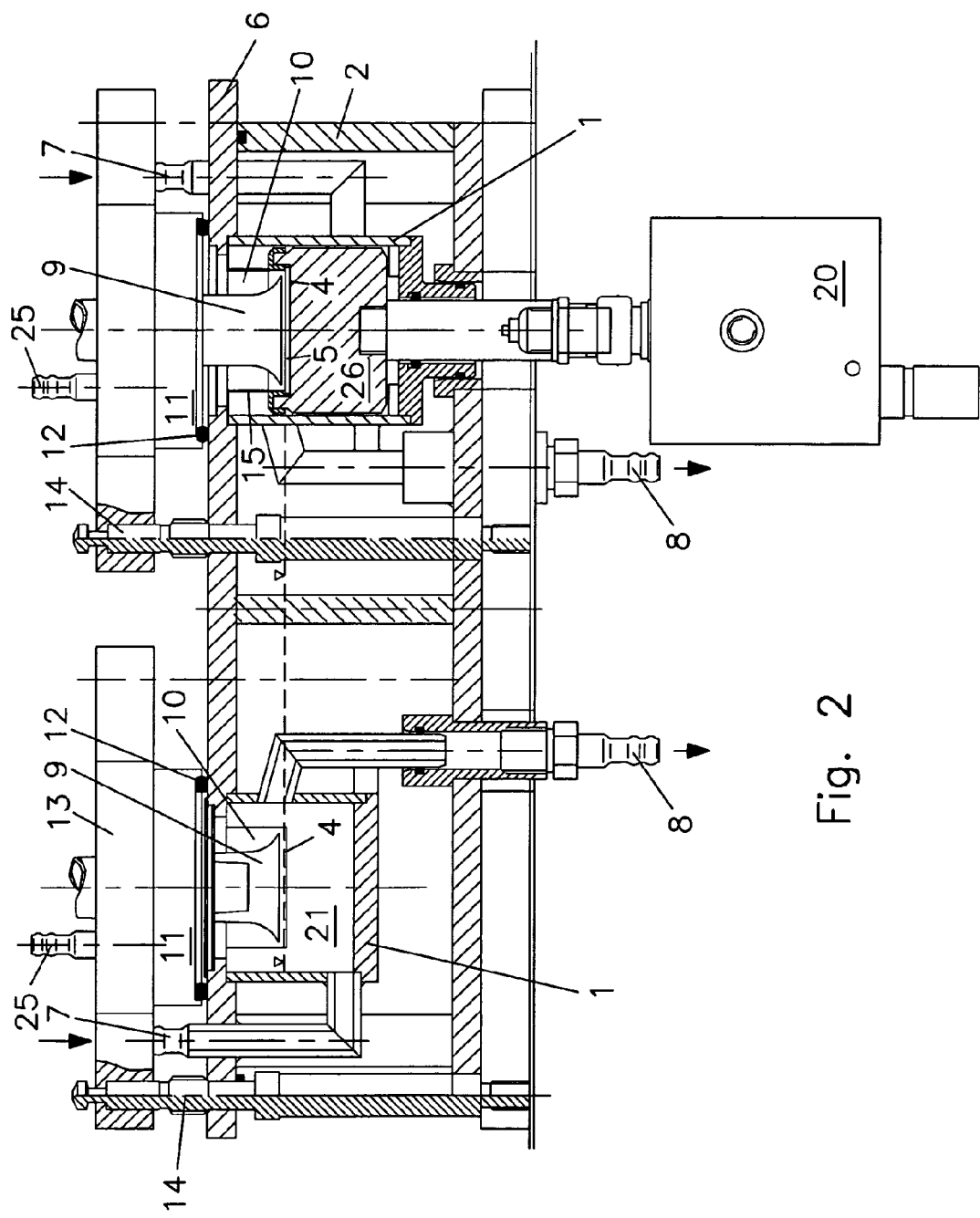

The sectional representation in accordance with FIG. 2 illustrates the topographic configuration of two exposure chambers 1 disposed on sectional plane A-A, the exposure chamber 1 located on the right equipped with the aforementioned quartz oscillator 5 as a quartz microscale on an additional mass 26 as a carrier underneath deposition surface 4, is conceived for measuring superfine particle masses. In the exemplary embodiment, quartz oscillator 5 is set into a recess of mass 26 and is pressed from below against an eye-nut screw connection by springs (not shown in detail) that are integrated in the mass. At the same time, the springs are used for electrically contacting the electrodes of the quartz oscillator (compare the Operation and Service Manual of the QCM50 and 100 type system of the firm Stanford Research Systems, Inc., Sunnyvale, Calif., in particular Chapter 1.6, FIG. 3, Contact Springs). The mass and eye-nut screw connection are then manufactured, for example, from an electrical insulator, such as plastic, for instance, Teflon.

The eye-nut screw connection, together with a collar 15 placed thereon, geometrically limits the through-flow volumes, in particular in the area of suction volume 10, in the manner that the vertical sides of Transwell insert 3 geometrically limit the exposure chamber located on the left. In any case, the through-flow volumes are geometrically adapted to one another, are limited by walls and fluid guides having the same topographies, for example, also by the same material surfaces, and are identical to the greatest degree possible. An oscillator 20 is used for driving the quartz microscale and for acquiring measurement data therefrom.

In an embodiment of the present invention, the exposure chambers are introduced from above into openings in a cover plate 6 of housing 2 and arranged in parallel to one another. Provided that they are not equipped with a quartz oscillator (compare FIGS. 3a and b), they each have an inlet 7 and an outlet 8 for a nutrient medium, in each case for a nutrient media volume 21 underneath the deposition surfaces, for supplying the cell cultures forming the deposition surfaces. Outlet 8 is configured in exposition chamber 1 to form a flow-off edge in order to always ensure a constant filling level of the nutrient medium in nutrient media volume 21 and thus a wetting and a supplying of the cell culture from below (compare also FIG. 3a).

FIG. 2 shows one inlet and outlet per illustrated exposure chamber. However, the exposure chamber shown on the right having a quartz oscillator does not have these itself, rather the inlet and the outlet are shown for the exposure chamber configured behind it that does not have a quartz oscillator (compare FIGS. 1 and 3b).

In an embodiment of the present invention in accordance with FIG. 1 through 3b, the exposure chamber having a quartz oscillator does not have any nutrient media volume 21. The space provided for that purpose is required for placement of mass 26. Thus, deposition surfaces 4 on quartz oscillator 5 are also not accessible to a nutrient medium from below. For this reason, the deposition surfaces on the quartz oscillator are made of, for example, a low-damping material having a surface topography that corresponds to that of a cell culture surface.

In addition, one aerosol feed 9 discharges from above into each exposure chamber 1. These direct the aerosol stream over the deposition surfaces, thereby inducing a localized emission onto the same that, for example, emanates radially from the middle of the deposition surface and is uniformly outwardly distributed. The aerosol stream is collected, in turn, from the deposition surface and removed by way of a suction volume 10 that discharges into ring channel 22 (compare the sectional representations in FIGS. 3a and b). The suction removal, for example, includes a ring channel 22 having an aerosol suction 25, as well as a multiplicity of passages (connecting channels 18) leading to suction volume 10 in cover 11 around the deposition surface for the purpose of radially removing the aerosol stream by suction. The deposition surface, aerosol feed and suction volume are, for example, configured axisymmetrically and are disposed mutually concentrically.

Deposition surfaces 4 of all exposure chambers 1 extend in parallel to cover plate 6 on a plane and, once cover 11 and aerosol feed 9 are lifted for each exposure chamber, are also accessible from above through the openings of the cover plate. To prevent a partial aerosol flow, the exposure chambers are each sealed at the top by one sealing ring 12 between cover 11 and cover plate 6. The covers are pressed via a pressure plate 13 onto exposure chambers 1. The pressure plate is supported on flange bolts 14 that are set into housing 2 and is fixed in position via quick-acting closures (not shown).

The sectional representations of the exposure chambers shown in FIG. 2 are reproduced in detail in FIGS. 3a and b.

FIG. 3a shows an exposure chamber without a microscale. Deposition surface 4 extends over the bottom area of Transwell insert 3, which is introduced from above into exposure chamber 1 and is centered and held by an outwardly bent beaker rim that engages under the cover. Inlet 7 for a nutrient medium leads into nutrient media volume 21 underneath the deposition surface (i.e., the cell cultures), where entire deposition surface 4 is wetted from below, and exits the volume via outlet 8. The superfine particle masses are directed as aerosol from above through aerosol feed 9, which is concentrically disposed about axis of symmetry 16, onto deposition surface 4. The inside of Transwell insert 3 outside of downwardly increasingly widening discharge region 17 of aerosol feed 9 forms suction volume 10 that is concentrically disposed in an annular shape about the same, including a multiplicity of connecting channels 18 that are concentrically disposed about the aerosol feed and discharge into annular channel system 22. Discharge region 17 widens conically downwardly or, for example,—as shown—in a trumpet shape and, over its entire periphery, forms a circumferential annular gap 19 of a constant width with deposition surface 4.

FIG. 3b shows an exposure chamber that is equipped with a quartz oscillator 5 as a sensing element of a quartz microscale. The area above deposition surface 4 is identical in its structure, dimensions and method of functioning to the aforementioned exposure chamber without a microscale that is shown in FIG. 3a. The deposition surface is, for example, formed by the surface of quartz oscillator 5 which, in turn, fills the volume underneath the deposition surface and is connected at the bottom to oscillator 20 (compare FIG. 2).

The efficiency of the deposition onto the deposition surfaces is able to be selectively influenced by means for producing a potential difference between the particles, which are contained in the gas, and deposition surfaces 4. One option provides for using means for ionizing these superfine particle masses in the aerosol, for example, already prior to the entry thereof into aerosol feed 9. The ionization can, for example, be carried out electrically or photonically, in individual cases, also radioactively, it being possible for the ionization to be selectively controlled or accelerated by additives to be added to the aerosol, for example, by additives acting as charge-transfer agents. To avoid a premature deposition of superfine particles, for example in the aerosol feed, the electrical potential difference between ionized superfine particles in the aerosol and the aerosol feed should be kept to a minimum. To increase the deposition rates of the ionized particles on the deposition surfaces, an electric field can then be established between these and discharge region 17 of the aerosol feed, for example, in annular gap 19.

If the superfine particle masses are composed of a plurality of different particle fractions, they can be separated in two different ways due to the aforementioned selective ionization. On the one hand, selectively ionized particle fractions in an electric field can be separated prior to the entry thereof into the device. On the other hand, a separation of the ionized particle fractions can be significantly selectively increased by application of the aforementioned electric field between deposition surface 4 and discharge region 17.

In the same way, it is possible to selectively influence the separation of particle fractions by applying a temperature difference between the particles in the aerosol and deposition surfaces 4. For example, heating the deposition surface allows specific fractions to be more readily vaporized thereon. Moreover, the temperature significantly influences the dynamics of the physical, chemical and biological interactions between separated particles and the deposition surfaces and thus selectively influences the deposition kinetics of individual particle fractions.

Alternative means for cooling deposition surface 4 and/or for heating the particles in the aerosol (for example, by a device connected upstream of aerosol feed 9) produce a flow of warmer particle masses over a colder deposition surface. Gaseous components thus also, for example, condense on the deposition surface.

If the device is used for the in vitro analyses mentioned at the outset of superfine dust deposits (dust, pharmaceuticals, drugs, other agents, spores, viruses or bacteria, etc.) or biochemical or biophysical interactions on bioassays, i.e., on biological or biologically active surfaces, then the deposition surfaces can, for example, be made of a biofilm or a cell culture.

To ensure a constant temperature of, for example, 37° C. for the aforementioned in vitro analyses, such as, for example, also toxicological applications in all exposure chambers, housing 2 can be flooded with a tempering medium, such as water or oil, for example, via an inlet and outlet for tempering 23, respectively, 24 (compare FIG. 1). The tempering medium fills the inner volume of the housing. For example, for a selective tempering of the deposition surfaces (indirectly by the nutrient medium in nutrient media volume 21 or mass 26), the liquid level of the tempering medium can, for example, be adjusted to the height of the deposition surfaces (compare the dashed horizontal line in FIG. 2).

The present invention is not limited to embodiments described herein; reference should be had to the appended claims.

LIST OF REFERENCE NUMERALS

1 exposure chamber
2 housing
3 Transwell insert
4 deposition surface
5 quartz oscillator
6 cover plate
7 inlet for nutrient medium
8 outlet for nutrient medium
9 aerosol feed
10 suction volume
11 cover
12 sealing ring
13 pressure plate
14 flange bolt
15 collar
16 axis of symmetry
17 discharge region
18 connecting channel
19 annular gap
20 oscillator
21 nutrient media volume
22 ring channel
23 inlet for tempering
24 outlet for tempering
25 aerosol suction
26 mass

The invention claimed is:

1. A device for measuring superfine particle masses, the device comprising:

a quartz oscillator; and an exposure system having at least two measuring chambers, each of the at least two measuring chambers having a same geometry, and each of the at least two measuring chambers containing a deposition surface for particles, and an aerosol feed directed at the respective deposition surface configured to feed an aerosol onto the respective deposition surface;

wherein a respective deposition surface of a first of the at least two chambers is disposed on the quartz oscillator and a respective deposition surface of a second of the at least two chambers is not disposed on a quartz oscillator.

2. The device as recited in claim 1, wherein each feed and respective deposition surface are configured so as to deflect the aerosol over at least one of the respective deposition surface.

3. The device as recited in claim 1, further comprising a suction volume disposed around at least one of the respective aerosol feeds.

4. The device as recited in claim 3,
wherein at least one of the respective aerosol feeds includes a discharge region having an expanded discharge cross section, the expanded discharge cross section, over a periphery thereof, having a constant distance to the respective deposition surface and forming a peripheral gap orifice; and
wherein the suction volume is disposed concentrically about the respective aerosol feed.

5. The device as recited in claim 4, wherein the discharge region is disposed axially symmetrically about an axis of symmetry and widens in a direction along the axis of symmetry.

6. The device as recited in claim 5, wherein the discharge region widens in a shape of a trumpet or conically.

7. The device as recited in claim 1, wherein the particles are contained in the aerosol, and further comprising a potential difference device configured to produce a potential difference between the particles contained in at least one of the aerosol and the respective deposition surfaces.

8. The device as recited in claim 7, wherein the potential difference device includes an ionizing device disposed upstream of the respective aerosol feed and configured to ionize the particles.

9. The device as recited in claim 1, further comprising an electric field generating device configured to generate an electric field between at least one of the respective aerosol feeds and the respective deposition surface.

10. The device as recited in claim 1, wherein the particles are contained in the aerosol and further comprising a temperature difference device configured to produce a temperature difference between the particles and the at least one of the respective deposition surfaces.

11. The device as recited in claim 10, wherein the temperature difference device is disposed upstream of the respective aerosol feed and includes at least one of a cooling device configured to cool the respective deposition surface and a heating device configured to heat the particles.

12. The device as recited in claim 1, wherein at least one of the deposition surfaces is not disposed on the quartz oscillator and is formed by at least one of a biofilm and a cell culture.

* * * * *